United States Patent [19]
Guillonneau et al.

[11] Patent Number: 5,698,567
[45] Date of Patent: Dec. 16, 1997

[54] HETEROCYCLIC SPIRO COMPOUNDS

[75] Inventors: Claude Guillonneau, Clamart; Yves Charton, Sceaux; Gilbert Regnier, Chatenay Malabry; Emmanuel Canet, Paris; Michel Lonchampt, Chevilly Larue, all of France

[73] Assignee: Adir Et Compagnie, Courbevoie, France

[21] Appl. No.: 649,020

[22] Filed: May 16, 1996

[30] Foreign Application Priority Data

May 17, 1995 [FR] France ............... 95 05833

[51] Int. Cl.$^6$ ............... A61K 31/44; C07Q 491/10
[52] U.S. Cl. ............... 514/278; 546/19
[58] Field of Search ............... 546/19; 514/278

[56] References Cited

U.S. PATENT DOCUMENTS 3,399,192  8/1968  Regnier ............... 546/19

FOREIGN PATENT DOCUMENTS

0479631A1  4/1992  European Pat. Off. .

OTHER PUBLICATIONS

Takai et al., Chemical and Pharmaceutical Bulletin, 33, No. 3, 1985, Tokyo, Japan, 1129–1139.

European Search Report for EP 96401029 of Aug. 7, 1996.

*Primary Examiner*—Alan L. Rotman
*Attorney, Agent, or Firm*—The Firm of Gordon W. Hueschen

[57] ABSTRACT

The invention provides new compounds pertaining to the class of:
aryl methoxy phenyl alkyl heterocyclic spiro compounds, enantiomers, diastereoisomers and physiologically-tolerable salts thereof.

For example:
8-{2-[3-quinol-2-yl methoxy)phenyl]ethyl}-3,8-diaza-1-oxa-2-oxo spiro[4,5]decane is described.

Medicinal products containing the same are useful in the treatment of any pathology involving modifications of leukotriene metabolism.

10 Claims, No Drawings

HETEROCYCLIC SPIRO COMPOUNDS

The present invention relates to new heterocyclic spiro compounds.

It relates especially to heterocyclic spiro compounds of formula I:

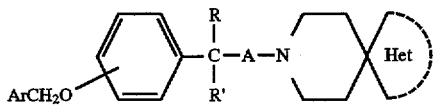

in which:

Ar represents:
  a) a mono- or bi-cyclic aromatic hydrocarbon radical that is optionally substituted by one or more substituents selected from halogen atoms and the radicals $(C_1-C_5)$alkyl, $(C_1-C_5)$-alkoxy, trifluoromethyl and phenyl, or
  b) a mono- or bi-cyclic heterocyclic radical that contains from 1 to 3 hetero atoms selected from the atoms oxygen, nitrogen and sulphur and that is optionally substituted by one or more substituents selected from halogen atoms and the radicals $(C_1-C_5)$alkyl, $(C_1-C_5)$-alkoxy, trifluoromethyl and phenyl;

R represents a hydrogen atom or a hydroxy radical;

R' represents a hydrogen atom or a radical selected from the radicals straight- or branched-chained $(C_1-C_5)$alkyl, phenyl, phenyl-$(C_1-C_5)$alkyl, $(C_3-C_8)$cycloalkyl and $(C_3-C_8)$-cycloalkyl-$(C_1-C_5)$alkyl, each of those radicals being unsubstituted or substituted by one or more substituents selected from halogen atoms and the radicals $(C_1-C_5)$alkyl, $(C_1-C_5)$alkoxy and trifluoromethyl; or R and R' together with the carbon atom to which they are bonded represent a carbonyl group;

A represents:
  a single bond,
  a carbonyl group, or
  a straight hydrocarbon chain having from 1 to 5 carbon atoms that may optionally contain an oxygen atom and/or be optionally substituted by one or two substituents selected from halogen atoms and the radicals $(C_1-C_5)$alkyl, $(C_1-C_5)$alkoxy and oxo; and

represents a 5-membered heterocycle containing 1 to 4 hetero atoms selected from the atoms oxygen, nitrogen and sulphur, which heterocycle is unsubstituted or substituted by one or two substituents selected from the radicals $(C_1-C_5)$alkyl, $(C_1-C_5)$alkoxy, hydroxy, oxo, thio, amino, thioxo, amino-$(C_1-C_5)$alkyl, $(C_1-C_5)$alkylamino-$(C_1-C_5)$alkyl and di$(C_1-C_5)$alkylamino-$(C_1-C_5)$alkyl.

Some compounds of formula I contain one or more asymmetric atoms and can therefore be in the form of enantiomers or diastereoisomers, which likewise form part of the present invention.

Likewise, compounds of formula I containing one or more amine functions can be converted into addition salts with pharmaceutically acceptable acids, such as, for example, hydrochloric acid and fumaric acid. Those salts are, as such, included in the present invention.

The closest prior art to the present invention is illustrated by U.S. Pat. No. 3,399,192, which relates to spiro[4,5] decane compounds of the formula:

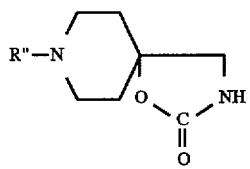

in which R'' represents inter alia a phenylalkyl radical in which:

the phenyl moiety can be substituted but never by the radical $ArCH_2O-$ that is present in formula I, and the alkyl moiety may optionally contain an oxygen atom or a hydroxy radical.

The said spiro[4,5]decane compounds are antagonists of some chemical mediators, such as serotonin, histamine and bradykinin.

The compounds of the present invention differ from the spiro[4,5]decane compounds defined above both in their chemical structure and in their pharmacological and therapeutic activity, which is a result of their inhibitory effect on the enzyme 5-lipoxygenase.

The present invention relates also to a process for the preparation of compounds of formula I, characterised in that:

A) a compound of formula II:

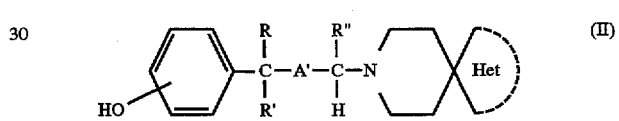

in which:

R, R' and

are as defined above,

A' represents:
  a single bond, or
  a straight hydrocarbon chain having from 1 to 4 carbon atoms that may optionally contain an oxygen atom and/or be optionally substituted by one or more substituents selected from halogen atoms and the radicals $(C_1-C_5)$alkyl, $(C_1-C_5)$alkoxy, hydroxy and oxo, and R'' represents a hydrogen atom or a linear or branched $(C_1-C_4)$alkyl radical, is reacted with a compound of formula III:

Ar-CH$_2$-X (III)

in which:

Ar is as defined above, and

X represents a halogen atom, such as a chlorine or bromine atom, to obtain a compound of formula Ia:

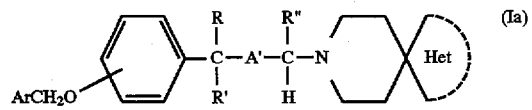

in which Ar, R, R', A', R" and

are as defined above; or
B) a compound of formula IV:

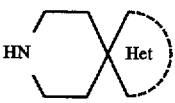

in which

is as defined above, is reacted
a) either with a compound of formula V:

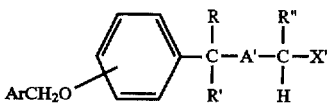

in which:
Ar, R, R', A' and R" are as defined above, and
X' represents a halogen atom, such as, for example, a bromine or chlorine atom, or a tosyloxy or mesyloxy group, to obtain a compound of formula Ia defined above;
b) or with a compound of formula VI:

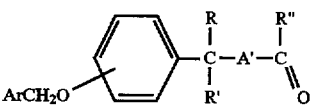

in which Ar, R, R', A' and R" are as defined above, in the presence of a reducing agent, such as, for example, a boron hydride, to obtain a compound of formula Ia defined above;
c) or with a compound of formula VII:

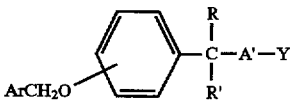

in which:
Ar, R, R' and A' are as defined above, and
Y represents —COOH or COCl, to obtain a compound of formula Ib:

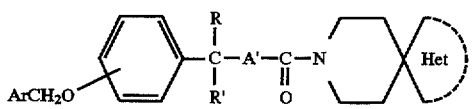

in which Ar, R, R', A' and

are as defined above;

d) or with a compound of formula VIII:

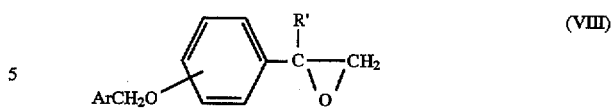

in which Ar and R' are as defined above, to obtain a compound of formula Ic:

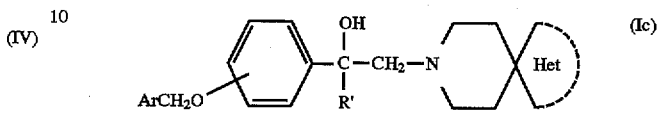

in which Ar, R' and

are as defined above.

The totality of the compounds of formulae Ia, Ib and Ic forms the totality of the compounds of formula I.

It is especially advantageous to react the compounds of formulae II and III in a solvent, such as, for example, methyl ethyl ketone, dimethylformamide or acetonitrile, at a temperature of from 50° to 100° C., in the presence of an acceptor for the hydracid formed during the reaction.

There may be used as the hydracid acceptor, for example, an alkali metal carbonate, such as potassium carbonate, in the presence of an alkali metal iodide, or triethylamine.

The reaction of compounds IV and V is advantageously carried out in a solvent, such as, for example, acetone, acetonitrile or dimethylformamide, at a temperature of from 50° to 120° C., in the presence of an acceptor for the hydracid formed during the reaction. There may be used as the acceptor, for example, an excess of the compound of formula IV, dimethylaminopyridine or triethylamine.

The reaction of the compounds of formulae IV and VI can be carried out in an aprotic solvent, such as methylene chloride or tetrahydrofuran, in the presence of a reducing agent, such as sodium triacetoxyborohydride, at a temperature of from 15° to 45° C.

It is also possible to condense the compounds of formulae IV and VI in an aromatic solvent, such as toluene, in the presence of an acid catalyst, such as 4-methylphenylsulphonic acid. The enamine formed as intermediate can be reduced either using a chemical reducing agent, such as sodium cyanoborohydride, or by hydrogenation in a low-boiling alcohol, such as ethanol, in the presence of a catalyst, such as palladium-on-carbon or Raney nickel.

The reaction of the compounds of formulae IV and VII is carded out:
either, when Y represents COOH, in the presence of a coupling agent, such as dicyclohexylcarbodiimide in dimethylformamide, or the cyclic arthydride of 1-propylphosphonic acid in accordance with the method of H. Wissmann and H. J. Kleiner, Angew. Chem. Int. Ed. Engl. 19 (1980) N° 2, p. 133;

or, when Y represents COCl, in the presence of a hydracid acceptor, such as triethylamine or dimethylaminopyridine, in an aprotic solvent, such as ether, tetrahydrofuran, methylene chloride or dimethylformamide, or in a basic solvent, such as pyridine.

The reaction of the compounds of formulae IV and VIII is advantageously carried out in a low-boiling alcohol, such as methanol or ethanol, at a temperature of from 40° to 100° C., optionally in the presence of a Lewis acid, such as boron trifluoride. The starting materials used are either known products or products prepared by customary methods starting from known compounds.

Accordingly, the compounds of formula II are obtained: either by reacting a compound of formula IX:

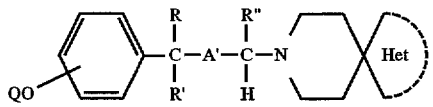
(IX)

in which R, R', R" and X are as defined above, with a compound of formula IV defined above, in a polar aprotic solvent, such as, for example, acetonitrile or methyl ethyl ketone, in the presence of a hydracid acceptor, which may be an excess of the compound of formula IV or an alkali metal carbonate;

or by deprotecting a compound of formula X:

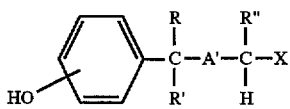
(X)

in which:

R, R', R", A' and

are as defined above, and

Q is a labile protecting group, such as, for example, a methyl or benzyl radical.

The deprotection can be carried out in the presence of a Lewis acid, such as boron tribromide, in an aprotic solvent, such as methylene chloride.

When Q is a benzyl radical, the deprotection can also be carried out by hydrogenation in the presence of a hydrogenation catalyst, such as palladium-on-carbon or palladium hydroxide-on-carbon, in a low-boiling alcohol, such as, for example, ethanol.

The compounds of formula III are known products that are described in the literature and are generally available commercially.

The compounds of formula IV used in the synthesis of the compounds mentioned by way of example were prepared by methods described in the literature and listed in the Table below:

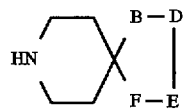

| B | D | E | F | Physical characteristics | Method of preparation |
|---|---|---|---|---|---|
| $CH_2$ | N—H | C=O | O | M.p.$_{(K)}$: 202° C. | G. REGNIER et al. Chimie Thérapeutique (1969) (3), 185–194 |
| —CH(CH$_3$)— | N—H | C=O | O | M.P.$_{(cap)}$: 245–246° C. | J. MAILLARD et al. Chimie Thérapeutique (1973) (4), 393, 397 |
| O | $CH_2$ | $CH_2$ | O | | Debenzylation of the corresponding 8-benzylated compound |
| $CH_2$ | O | C=O | NH | Hydrochloride M.p.$_{(cap)}$: 217–218° C. | Debenzylation of the corresponding 8-benzylated compound. M.p.$_{(cap)}$: 168–170° C. |
| $CH_2$ | N(CH$_2$)$_2$—C$_6$H$_5$ | C=O | O | Hydrochloride M.p.$_{(cap)}$: 246–247° C. | Debenzylation of the corresponding 8-benzylated compound. M.p.$_{(K)}$: 153° C. |
| $CH_2$ | N—CH$_3$ | C=O | O | Hydrochloride M.p.$_{(cap)}$: 260° C. | Debenzylation of the corresponding 8-benzylated compound. M.p.$_{(cap)}$: 130° C. |
| $CH_2$ | N—C$_2$H$_5$ | C=O | O | Hydrochloride M.p.$_{(cap)}$: 230° C. | Debenzylation of the corresponding 8-benzylated compound. M.p.$_{(K)}$: 95° C. |
| $CH_2$ | N—(CH$_2$)$_2$—N(CH$_3$)$_2$ | C=O | O | Dihydrochloride M.p.$_{(cap)}$: 250° C. (dec.) | Debenzylation of the corresponding 8-benzylated compound. M.p.$_{(cap)}$: 101° C. |
| $CH_2$ | C=O | NH | C=O | M.p.$_{(K)}$: 245° C. | Debenzylation of the corresponding 8-benzylated compound. M.p.$_{(K)}$: 187° C. |
| $CH_2$ | C=O | NH | $CH_2$ | Hydrochloride M.p.$_{(cap)}$: 250° C. (dec.) | Debenzylation of the corresponding 8-benzylated compound. M.p.$_{(cap)}$: 152° C. G. CIGNARELLA S. VILLA J. Heterocyclic Chemistry (1993), Vol. 30, No 5, 1357. |

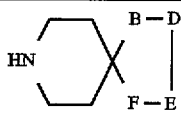

| B | D | E | F | Physical characteristics | Method of preparation |
|---|---|---|---|---|---|
| CH$_2$ | NH | C=S | O | M.p.$_{(K)}$: 241° C. | Detritylation of the corresponding 8-tritylated compound. M.p.$_{(cap)}$: 248–250° C. |

The compounds of formula V were obtained by reacting a compound of formula XI:

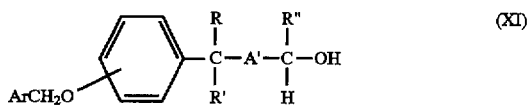

in which Ar, R, R', A' and R" are as defined above, with a halogenation reagent, such as thionyl chloride, or phosphorus pentachloride, or with triphenylphosphine, in the presence of CCl$_4$, or in the presence of bromine in acetonitrile in accordance with the method of J. Hooz et al., Can. J. Chem. 46, 86–87 (1968) or of Schaeffer et al., Org. Synth. coll. Vol. V, 249, or with a sulphonic acid halide, such as tosyl chloride, in a basic solvent, such as pyridine, at a temperature of from 5° to 25° C.

The compounds of formula XI are themselves obtained by reacting a compound of formula XII:

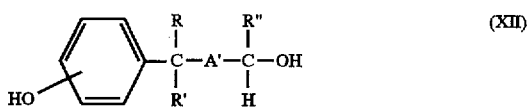

in which R, R', A' and R" are as defined above, with a compound of formula III defined above.

Such a reaction can be carried out:

either in amides or ketones having low molecular weights, such as, for example, dimethylformamide or methyl ethyl ketone, in the presence of an alkali metal carbonate, such as potassium carbonate, or of an organic base, such as triethylamine, at a temperature of from 10° to 70° C., or in methylene chloride, in the presence of water, of an alkali metal carbonate, such as potassium carbonate, and of a quaternary ammonium halide, such as Adogene®, at a temperature of from 10° to 40° C.

With regard to the compounds of formula VI that can be used in the synthesis of the compounds mentioned by way of example below: the compounds of formula VIa:

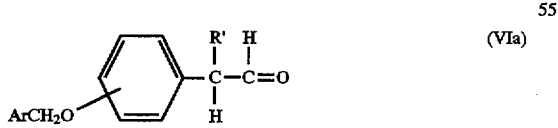

in which Ar and R' are as defined above, were obtained by isomerising, in the presence of a Lewis acid, a compound of formula VIII defined above, in accordance with the method described by E. J. Corey and M. Chaykovsky, J. Am. Chem. Soc. 87, 6, (1965).

The compounds of formula VIII are themselves obtained by reacting a compound of formula XIII:

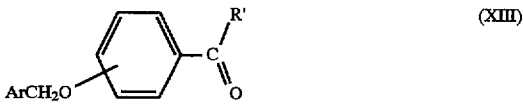

in which Ar and R' are as defined above, with trimethylsulphonium iodide or trimethylsulphoxonium iodide in dimethyl sulphoxide, in the presence of sodium hydride, in accordance with the method described by E. J. Corey and M. Chaykovsky, J. Am. Chem. Soc. 87, 6, (1965).

The compounds of formula XIII are obtained by reacting a compound of formula XIV:

in which R' is as defined above (which compound, depending upon the meaning of R', is either commercial or described in the literature), with a compound of formula III defined above, in a polar aprotic solvent, such as dimethylformamide, in the presence of a hydracid acceptor, such as potassium carbonate; the compounds of formula VIb:

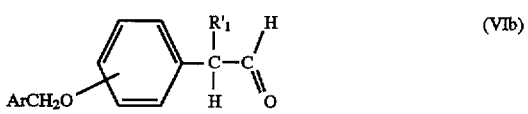

in which:

Ar is as defined above, and

R'$_1$ represents a hydrogen atom or a radical selected from the radicals phenyl-(C$_1$–C$_5$)alkyl, (C$_3$–C$_8$)cycloalkyl and (C$_3$–C$_8$)cycloalkyl-(C$_1$–C$_5$)alkyl, each of those radicals being unsubstituted or substituted by one or more substituents selected from halogen atoms and the radicals (C$_1$–C$_5$)alkyl, (C$_1$–C$_5$)alkoxy and trifluoromethyl, are obtained by reacting a compound of formula XV:

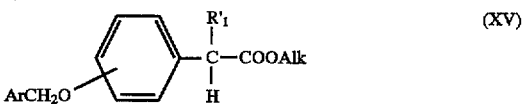

in which:

Ar and R'$_1$ are as defined above, and

Alk represents a (C$_1$–C$_5$)alkyl radical, with diisobutylaluminium hydride in accordance with the method of Muraki and Mukaiyama, Chem. Lett. (1975), 215.

Of the compounds of formula XV, those in which R'$_1$ represents hydrogen, that is to say those corresponding to formula XVa:

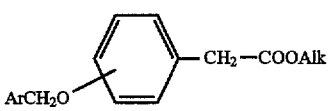
(XVa)

in which Ar and Alk are as defined above, were obtained by reacting the compounds of formula XVI:

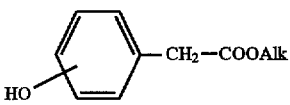
(XVI)

in which Alk is as defined above, (which compounds XVI are known products) with a compound of formula III defined above, the reaction being carded out in a polar aprotic solvent, such as dimethylformamide, in the presence of a hydracid acceptor, such as potassium carbonate; the compounds of formula XV in which $R'_1$ does not represent hydrogen, that is to say those corresponding to formula XVb:

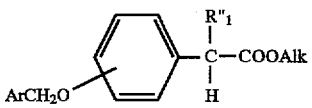
(XVb)

in which:
Ar and Alk are as defined above, and
$R''_1$ has the same meanings as $R'_1$ with the exception of hydrogen, are obtained by reacting a compound of formula XVa defined above with a halide of formula XVII:

$$R''_1\text{-}X \quad \text{(XVII)}$$

in which $R''_1$ and X are as defined above, the reaction being carried out in the presence of a strong base, such as, for example, sodium amide, in a suitable solvent, such as, for example, toluene.

The compounds of formula VII were synthesised from compounds of formula XVIII:

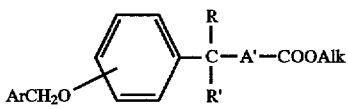
(XVIII)

in which Ar, R, R', A' and Alk are as defined above, which, when hydrolysed by means of an alkali metal hydroxide, such as, for example, sodium hydroxide, yield the compounds of formula VIIa:

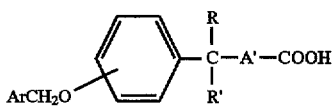
(VIIa)

in which Ar, R, R' and A' are as defined above, which, when treated with a customary reagent for converting a carboxylic acid into an acid halide; such as, for example, thionyl chloride or phosphorus pentachloride, yield the compounds of formula VIIb:

(VIIb)

in which Ar, R, R' and A' are as defined above.

The totality of the compounds of formulae VIIa and VIIb forms the totality of the compounds of formula VII.

The compounds of formula XVIII were themselves synthesised by reacting a compound of formula XIX:

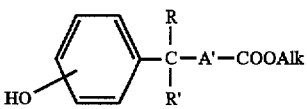
(XIX)

in which R, R', A' and Alk are as defined above, with a compound of formula III defined above in a polar aprotic solvent, such as dimethylformamide, in the presence of a hydracid acceptor, such as potassium carbonate.

The compounds of formula I so obtained can be purified either by flash chromatography on silica (Amicon 35–70 µ) using ethyl acetate or a mixture of methylene chloride and methanol as eluant, or by the formation of salts and crystallisation thereof.

Some compounds of formula I yield physiologically tolerable salts, which salts are, as such, included in the present invention.

The compounds of the present invention have valuable pharmacological and therapeutic properties.

In particular, the compounds have been shown to have an inhibitory activity on the enzyme 5-lipoxygenase both in vitro and ex vivo.

5-Lipoxygenase is the enzyme for the first stage of the metabolism of arachidonic acid, leading to synthesis of leukotrienes. The first stage results in the synthesis of 5-hydroperoxyeicosatetraenoic (5(S)-HPETE), which is converted into an unstable epoxide, leukotriene A4 (LTA4). LTA4 is converted by enzymatic hydration into leukotriene B4 or, by conjugation with glutathion, into leukotriene C4 which, by successive proteolytic cleavages, will lead to the formation of LTD4 and LTE4 (see Samuelsson B. and C. D. Funk. *Enzymes Involved in the Biosynthesis of Leukotrienes B4. The Journal of Biochemistry*, Vol. 264, N° 33, p. 19469–19472, 1989). The above-mentioned leukotrienes are lipid substances which play an important part in the physiopathology of various diseases.

Inhibiting 5-lipoxygenase, the first stage leading to the synthesis of leukotrienes, therefore constitutes a therapeutic approach aimed at limiting the effects of those lipids. Compounds having 5-lipoxygenase-inhibiting activity can therefore be used in the treatment of human diseases in which the role of leukotrienes has been mentioned, such as, especially, in dermatological pathologies such as eczema and psoriasis (see Lewis R. A., Austen K. F. and R. J. Soberman, *Leukotrienes and Other Products of the 5-Lipoxygenase Pathway*. The New England Journal of Medicine, Vol. 323, N° 10, p. 645–655, 1990).

The present invention relates also to pharmaceutical compositions comprising as active ingredient a compound of formula I, or a physiologically tolerable salt thereof, in admixture or in association with one or more suitable pharmaceutical excipients, such as, for example, glucose, lactose, starch, ethylcellulose, magnesium stearate or cocoa butter.

The pharmaceutical compositions are generally presented in dosage unit form. They can be administered in therapeutic doses ranging from 0.001 mg to 25 mg of active ingredient per kg of body weight intravenously and from 0.01 mg to 100 mg of active ingredient per kg of body weight orally.

The Examples which follow illustrate the present invention, melting points being determined using a Kofler hot plate (K) or by means of a capillary tube (cap).

EXAMPLE 1

8-{2-[3-(quinol-2-ylmethoxy)phenyl]ethyl}-3,8-diaza-1-oxa-2-oxospiro[4,5]decane

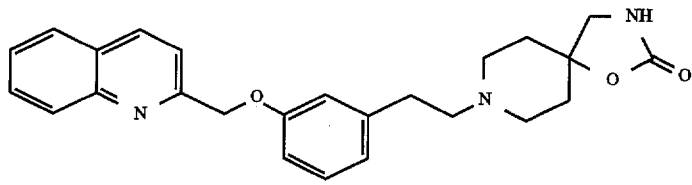

12.5 g (0.058 mol) of 2-chloromethylquinoline hydrochloride, 9.8 g of 3-hydroxyphenylethanol, 8 g of potassium carbonate, 8 g of sodium hydroxide, 150 ml of methylene chloride and 5 g of Adogene 624 are introduced into a flask. Stirring is carded out at room temperature for 16 hours. The mixture is washed with water, dried over sodium sulphate and concentrated to dryness. The residue is chromatographed on 1.5 litres of silica using a methylene chloride/methanol mixture (98/2) as eluant. There are obtained 8.6 g of 2-[3-(quinol-2-ylmethoxy)-phenyl]ethanol. Yield: 53%.

8.6 g of 2-[3-(quinol-2-ylmethoxy)phenyl]ethanol are dissolved in 200 ml of methylene chloride. There are added 9.8 g of tdphenylphosphine and then, at 10° C., 1.9 g of bromine dissolved in 50 ml of methylene chloride. Stirring is carded out at room temperature for 16 hours. The mixture is concentrated to dryness and the residue is taken up in ether. The mixture is washed with a 10% sodium carbonate solution and dried over sodium sulphate. Concentration to dryness is carded out. The residue is chromatographed on 450 g of silica using methylene chloride as eluant. There are obtained 7.7 g of 1-bromo-2-[3-(quinol-2-yl-methoxy) phenyl]ethane. Yield: 72%.

2.4 g of 1-bromo-2-[3-(quinol-2-ylmethoxy)phenyl] ethane, 2.2 g of 3,8-diaza-1-oxa-2-oxospiro[4,5]decane, 0.4 g of potassium iodide and 100 ml of acetonitrile are introduced into a flask. The mixture is heated at reflux for 16 hours. Concentration to dryness is carried out. The residue is taken up in methylene chloride. The mixture is washed with a 10% sodium carbonate solution and dried over sodium sulphate. Concentration to dryness is carded out and the residue is crystallised from a mixture of ethanol and ether. There are obtained 1.6 g of 8-{2-[3-(quinol-2-ylmethoxy)phenyl]ethyl}-3,8-diaza-1-2 -oxospiro[4,5] decane, m.p.(cap): 132°–136° C. Yield: 54%.

EXAMPLE 2 TO 4

By proceeding as described in Example 1, the compounds of the following Examples were prepared:
2) 8-{2-[4-(quinol-2-ylmethoxy)phenyl]ethyl}-3,8-diaza-1-2-oxospiro[4,5]decane, m.p.(cap): 186°–189° C.
3) 8-{2-[4-[(1-methyl-2-oxo-1H-quinol-6-yl)methoxy]phenyl]ethyl}-3,8-diaza-1-oxa-2-oxospiro[4,5]decane, m.p.(cap): 228°–230° C.
4) 8-{2-[3-[(1-methyl-2-oxo-1H-quinol-6-yl)methoxy]phenyl]ethyl}-3,8-diaza-1-oxa-2-oxospiro[4,5]decane, m.p.(cap): 160°–162° C.

EXAMPLE 5

(R,S)-8-{2-hydroxy-2-[4-(quinol-2-ylmethoxy)phenyl]ethyl}-3,8-diaza-1-oxa-2-oxospiro[4,5]decane

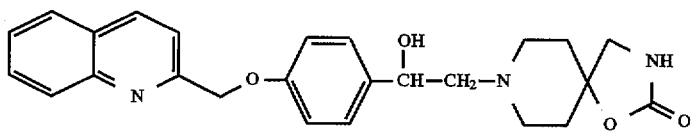

Step A 43.5 g (0.2 mol) of 4-bromoacetylphenol, 62.4 g (0.4 mol) of 3,8-diaza-1-oxa-2-oxospiro[4,5]decane and 1500 ml of methyl ethyl ketone are introduced into a flask. The mixture is heated at reflux for 14 hours. The mixture is cooled and the crystals are suction-filtered and washed with a 10% sodium carbonate solution and then with water. Drying is carried out at 50° C. under 67 Pa. There are obtained 34.8 g of 8-{2-(4-hydroxyphenyl)-2-oxoethyl}-3,8-diaza-1-oxa-2-oxospiro[4,5]decane, m.p.(cap): 250° C.

20 g of 8-{2-(4-hydroxyphenyl)-2-oxoethyl}-3,8-diaza-1-oxa-2-oxospiro [4,5]decane, 69 ml of N hydrochloric acid, 100 ml of methanol, 300 ml of water and 7 g of 5% palladium-on-carbon are introduced into a Parr hydrogenation apparatus. Hydrogenation is carded out under $7 \times 10^5$ Pa at room temperature. The catalyst is filtered off and concentration to dryness is carried out. The residue is taken up in water and rendered alkaline with sodium hydroxide, and the precipitate is suction-filtered, washed with water and dried at 50° C. under 67 Pa. There are obtained (R,S)-8-{2-hydroxy-2-(4-hydroxyphenyl)ethyl}-3,8-diaza-1-oxa-2-oxospiro[4,5]decane, m.p.(cap): 213°–214° C. Yield: 72%.

Step B

Preparation of the title compound.

1.47 g of (R,S)-8-{2-hydroxy-2-(4-hydroxyphenyl)ethyl}-3,8-diaza-1-oxa-2-oxospiro[4,5]-decane, 1.1 g of 2-chloromethylquinoline hydrochloride, 1.53 g of potassium carbonate and 50 ml of dimethylformamide are introduced into a three-necked flask. Stirring is carried out at room temperature for 16 hours, and then the mixture is concentrated to dryness. The residue is taken up in a 10% sodium carbonate solution. Extraction is then carded out with methylene chloride, and the extract is dried over sodium sulphate and concentrated to dryness. The residue is chromatographed on 200 g of silica using a methylene chloride/methanol mixture. (95/5) as eluant. The residue is recrystallised from ethanol to give 1 g of the title compound, m.p.(cap): 150°–155° C. Yield: 46%.

EXAMPLE 6

(R,S)-8-{2-phenyl-2-[4-(quinol-2-ylmethoxy)phenyl]ethyl}-3,8-diaza-1-oxa-2-oxospiro[4,5]decane

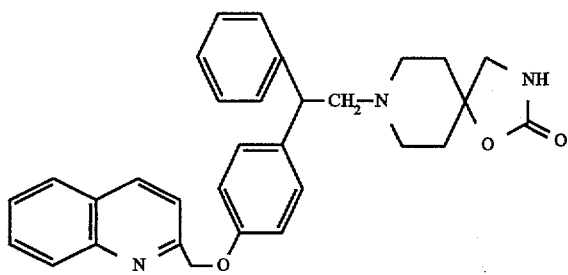

(60 g (0.3 mol) of 4-hydroxybenzophenone, 42 g of benzyl chloride, 45.6 g of potassium carbonate, 0.5 g of potassium iodide and 1 litre of dimethylformamide are introduced into a flask. Stirring is carried out at room temperature for 72 hours. The mixture is filtered and concentrated to dryness without exceeding 30° C. The residue is taken up in methylene chloride and washed with a 10% sodium carbonate solution and then with a saturated lithium chloride solution. The mixture is dried over sodium sulphate and concentrated to dryness. There are obtained 85 g of 4-benzyloxybenzophenone. Yield: 99%.

4.8 g of 60% sodium hydride previously washed with pentane are introduced into a three-necked flask. 26.4 g of trimethylsulphoxonium iodide are added, and 120 ml of dimethyl sulphoxide are added at room temperature over a period of 10 minutes. The mixture is stirred for 30 minutes, and 28.8 g of 4-benzyloxybenzophenone dissolved in 100 ml of dimethyl sulphoxide are added over a period of 10 minutes. The mixture is heated at 50° C. for 3 hours. 300 ml of water are added and extraction is carried out with ether. The ethereal phase is dried over sodium sulphate and concentrated to dryness. The residue is taken up in 300 ml of methylene chloride, and 6.8 ml of boron trifluoride etherate are added. The mixture is stirred at room temperature overnight and is hydrolysed. The organic phase is washed with water and dried over sodium sulphate. Concentration to dryness is carried out and the residue is chromatographed on 530 g of silica using a methylene chloride/cyclohexane mixture (50/50) as eluant. There are obtained 10.1 g of (R,S)-2-phenyl-2-(4-benzyloxyphenyl)acetaldehyde. Yield: 33%.

4.5 g (0.015 mol) of (R,S)-2-phenyl-2-(4-benzyloxyphenyl)acetaldehyde, 2.3 g of 3,8-diaza-1-oxa-2-oxospiro[4,5]decane and 100 ml of methylene chloride are introduced into a three-necked flask. 7.05 g of sodium triacetoxyborohydride are added at room temperature. The mixture is stirred for 16 hours and washed with a 10% sodium carbonate solution, and 100 ml of N hydrochloric acid are added. The mixture is suction-faltered and the precipitate is washed with water and then with ether. There are obtained 6.0 g of (R,S)-8-[2-(4-benzyloxyphenyl)-2-phenylethyl]-3,8-diaza-1-oxa-2-oxospiro[4,5]decane hydrochloride.

4.0 g of (R,S)-8-[2-(4-benzyloxyphenyl)-2-phenylethyl]-3,8-diaza-1-oxa-2-oxospiro[4,5]decane hydrochloride, 250 ml of methanol and 1 g of palladium hydroxide-on-carbon are introduced into a Parr hydrogenation apparatus. Hydrogenation is carried out at 50° C. under 4×10⁵ Pa. The catalyst is filtered off and concentration to dryness is carried out. The residue is dried at 20° C./67 Pa. There are obtained 4.0 g of (R,S)-8-[2-(4-hydroxyphenyl)-2-phenylethyl]-3,8-diaza-1-oxa-2-oxospiro[4,5]decane hydrochloride. Yield: 92%.

4.0 g of (R,S)-8-[2-(4-hydroxyphenyl)-2-phenylethyl]-3,8-diaza-1-oxa-2-oxospiro[4,5]decane hydrochloride, 2.7 g of 2-chloromethylquinoline hydrochloride, 3.45 g of potassium carbonate and 120 ml of dimethylformamide are introduced into a three-necked flask. Stirring is carried out at room temperature for 16 hours. The mixture is concentrated to dryness at a temperature below 35° C. The residue is taken up in methylene chloride. The mixture is washed with a sodium hydrogen carbonate solution and then with a lithium chloride solution. Drying is carried out over sodium sulphate. The residue is chromatographed on 400 g of silica using a methylene chloride/methanol mixture (97/3) as eluant.

The fractions that are of interest are concentrated to dryness. The residue is taken up in ethanol. The mixture is acidified to pH 5 with ethanol/hydrochloric acid. It is suction-filtered, washed with ethanol and dried at 40° C. under 67 Pa. There are obtained 3.6 g of (R,S)-8-{2-phenyl-2-[4-(quinol-2-ylmethoxy)phenyl]ethyl}-3,8-diaza-1-oxa-2-oxospiro[4,5]decane monohydrochloride. Yield: 59%. M-p. (cap): 242°–244° C.

EXAMPLES 7 TO 21

By proceeding as described in Example 6, the compounds of the following Examples were prepared:

7) (R,S)-8-{2-[4-(naphth-2-ylmethoxy)phenyl]-2-phenylethyl}-3,8-diaza-1-oxa-2-oxospiro[4,5]decane, m.p.(cap): 150°–152° C.

8) (R,S)-8-{2-(4-chlorophenyl)-2-[4-(quinol-2-ylmethoxy)phenyl]ethyl}-3,8-diaza-1-oxa-2-oxospiro[4,5]decane dihydrochloride (lyophilisate).

9) (R,S)-8-{2-phenyl-2-[4-(5-phenylpyrid-2-ylmethoxy)phenyl]ethyl}-3,8-diaza-1-oxa-2-oxospiro[4,5]decane, m.p.(cap: 166°–168° C.

10) (R,S)-8-{2-phenyl-2-[4-(quinol-2-ylmethoxy)phenyl]ethyl}-8-aza-1,4-dioxaspiro[4,5]decane dihydrochloride, m.p.(cap): 110° C. (dec).

11) (R,S)-8-{2-phenyl-2-[4-(quinol-2-ylmethoxy)phenyl]ethyl}-1,8-diaza-3-oxa-2-oxospiro[4,5]decane, m.p.(cap): 160°–162° C.

12) (R,S)-3-(2-phenylethyl)-8-{2-phenyl-2-[4-(quinol-2-ylmethoxy)phenyl]ethyl }-3,8-diaza-1-oxa-2-oxospiro[4,5]decane, m.p.(cap): 110°–112° C.

13) (R,S), (R,S)-4-methyl-8-{2-phenyl-2-[4-quinol-2-ylmethoxy)phenyl]ethyl}-3,8-diaza-1-oxa-2-oxospiro[4,5]decane, m.p.(cap): 156°–158° C.

14) (R,S)-8-{2-[4-(6-fluoroquinol-2-ylmethoxy)phenyl]-2-phenylethyl}-3,8-diaza-1-oxa-2-oxospiro[4,5]decane, m.p.(cap): 166°–168° C.

15) (R,S)-3-[2-dimethylamino)ethyl]-8-{2-phenyl-2-[4-(quinol-2-ylmethoxy) phenyl]ethyl}-3,8-diaza-1-oxa-2-oxospiro[4,5]decane trihydrochloride, m.p.(cap): 175° C. (dec).

16) (R,S)-3-methyl-8-{2-phenyl-2-[4-(quinol-2-ylmethoxy)phenyl]ethyl}-3,8-diaza-1-oxa-2-oxospiro[4,5]decane, m.p.(cap): 120°–122° C.

17) (R,S)-3-ethyl-8-{2-phenyl-2-[4-(quinol-2-ylmethoxy)phenyl]ethyl}-3,8-diaza-1-oxa-2-oxospiro[4,5]decane, m.p.(cap): 124°–126° C.

18) (R,S)-8-{2-phenyl-2-[4-(quinol-2-ylmethoxy)phenyl]ethyl}-2,8-diaza-1,3-dioxospiro[4,5]decane, m.p.(cap): 114°–116° C.

19) (R,S)-8-{2-phenyl-2-[4-(quinol-2-ylmethoxy)phenyl]ethyl}-3,8-diaza-1-oxa-2-thioxospiro[4,5]decane, m.p. (cap): 198°–200° C.

20) (R,S)-2-phenylethyl-8-{2-phenyl-2-[4-(quinol-2-ylmethoxy)phenyl]ethyl}-2,8-diaza-1,3-dioxospiro[4,5]decane, m.p.(cap): 123°–125° C.

21) R,S)-2-methyl-8-{2-phenyl-2-[4-(quinol-2-ylmethoxy)phenyl]ethyl}-2,8-diaza-1,3-dioxospiro[4,5]decane, m.p. (cap): 150°–152° C.

EXAMPLE 22

(R,S)-8-{(4-chlorophenyl)-[4-(quinol-2-ylmethoxy)phenyl]methyl}-3,8-diaza-1-oxa-2-oxospiro[4,5]decane dihydrochloride

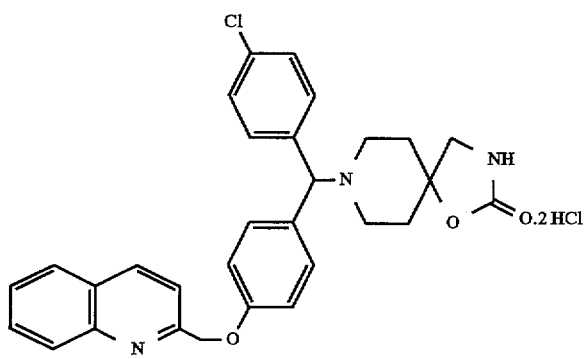

32 g of 4-chloro-4'-benzyloxybenzophenone and 350 ml of tetrahydrofuran are introduced into a three-necked flask. The mixture is cooled to 5° C., and 7.6 g of sodium borohydride dissolved in 20 ml of water are added. Stirring is carried out at 20° C. for 16 hours. The mixture is concentrated to dryness. The residue is taken up in methylene chloride, washed with a sodium hydrogen carbonate solution and dried over sodium sulphate. Concentration to dryness is carried out to give 32 g of (R,S)-(4-benzyloxy)-(4-chlorophenyl)methahol. Yield: 100%.

11 g (0.034 mol) of (R,S)-(4-benzyloxy)-(4-chlorophenyl)methanol and 200 ml of thionyl chloride are introduced into a three-necked flask. The mixture is heated at 50° C. for one hour. Concentration to dryness is carried out. Toluene is added and the mixture is concentrated again in order to remove the excess thionyl chloride. 11.7 g of 3,8-diaza-1-oxa-2-oxospiro[4,5]decane and 150 ml of toluene are added to the residue. Stirring is carried out at reflux for 16 hours. The mixture is concentrated to dryness. The residue is taken up in methylene chloride and washed with a sodium hydrogen carbonate solution. The mixture is dried over sodium sulphate and concentrated to dryness. There are obtained 12 g of (R,S)-8-[(4-chlorophenyl)-(4-benzyloxyphenyl)methyl]-3,8-diaza-1-oxa-2-oxospiro[4,5]decane. Yield: 75%.

12 g of (R,S)-8-[(4-chlorophenyl)-(4-benzyloxyphenyl)methyl]-3,8-diaza-1-oxa-2-oxospiro[4,5]decane, 100 ml of methylene chloride and 8.7 g of N-ethylmorpholine are introduced into a three-necked flask. The mixture is cooled to 5° C., and 55 ml of boron tribromide in 1N methylene chloride are added. The mixture is stirred at room temperature for 5 hours, and a further 55 ml of boron tribromide in methylene chloride are added. Stirring is carried out at room temperature for 24 hours. The mixture is cooled to 5° C. and hydrolysed with a sodium hydrogen carbonate solution until the pH is alkaline. The organic phase is dried over sodium sulphate and concentrated to dryness. The residue is chromatographed on 760 g of silica using a methylene chloride/methanol mixture (95/5) as eluant. There are obtained 3.5 g of (R,S)-8-[4-chlorophenyl-(4-hydroxyphenyl)methyl]-3,8-diaza-1-oxa-2-oxospiro[4,5]decane. Yield: 34%.

3.5 g of (R,S)-8-[4-chlorophenyl-(4-hydroxyphenyl)methyl]-3,8-diaza-1-oxa-2-oxospiro[4,5]decane, 3 g of potassium carbonate, 0.2 g of potassium iodide, 2.3 g of 2-chloromethylquinoline hydrochloride and 120 ml of dimethylformamide are introduced into a three-necked flask. Stirring is carried out at 60° C. for 16 hours. The mixture is concentrated to dryness. The residue is taken up in methylene chloride and washed with a 10% sodium carbonate solution and then with a saturated lithium chloride solution. The organic phase is dried over sodium sulphate. The residue is chromatographed on 760 g of silica using a methylene chloride/methanol mixture (97/3) as eluant. The fractions that are of interest are concentrated to dryness. Ethanolic hydrogen chloride is added to the residue. Crystals are seen to appear and are suction-filtered, washed with ether and dried at 40° C. under 67 Pa. There are obtained 4.8 g of (R,S)-8-{(4-chlorophenyl)-[4-(quinol-2-ylmethoxy)phenyl]methyl}-3,8-diaza- 1-oxa-2-oxospiro[4,5]decane dihydrochloride, m.p.(cap): 214°–216° C. Yield: 84%.

EXAMPLES 23 TO 27

By proceeding as described in Example 22, the compounds of the following Examples were prepared:

23) (R,S)-8-{[4-(naphth-2-ylmethoxy)phenyl]phenylmethyl}-3,8-diaza-1-2-oxospiro[4,5]decane, m.p. (cap): 126°–128° C.

24) (R,S)-8-{phenyl-[4-(quinol-2-ylmethoxy)phenyl]methyl}-3,8-diaza-1-oxa-2-oxospiro[4,5]decane, m.p. (cap): 184°–186° C.

25) (R,S)-8-{[4-(1-methyl-2-oxo-1H-quinol-6-ylmethoxy)phenyl]phenylmethyl}-3,8-diaza-1-oxa-2-oxospiro[4,5]decane, m.p.(cap): 162-20 –164° C.

26) (R,S)-8-{phenyl-[4-(5-phenylpyrid-2-ylmethoxy)phenyl]methyl}-3,8-diaza-1-oxa-2-oxospiro[4,5]decane, m.p.(cap): 190°–192° C.

27) (R,S)-8-{phenyl-[4-(6-fluoroquinol-2-ylmethoxy)phenyl]methyl}-3,8-diaza-1-oxa-2-oxospiro[4,5]decane, m.p.(cap): 200°–202° C.

EXAMPLE 28

8-{2-oxo-2-[4-(quinol-2-ylmethoxy)phenyl]ethyl}-3,8-diaza-1-oxa-2 -oxospiro[4,5]decane

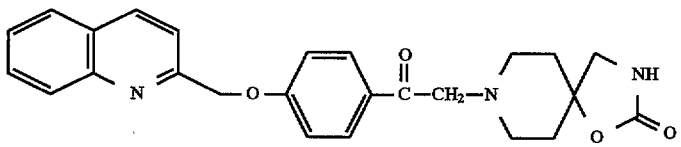

2.9 g of 8-[2-(4-hydroxyphenyl)-2-oxo]ethyl]-3,8-diaza-1-oxa-2-oxospiro [4,5]decane, 2.14 g of 2-chloromethylquinoline hydrochloride, 3 g of potassium carbonate, 0.1 g of potassium iodide and 100 ml of dimethylforraamide are introduced into a flask. Stirring is carried out at room temperature for 24 hours. The mixture is concentrated to dryness without heating. The residue is taken up in methylene chloride. The mixture is washed with a 10% sodium hydrogen carbonate solution and then with a saturated lithium chloride solution. It is dried over sodium sulphate and concentrated to dryness. The residue is chromatographed on 350 g of silica using a methylene chloride/methanol mixture (97/3) as eluant. The fractions that are of interest are concentrated to dryness and triturated in ethanol. Suction-filtration is carried out and the crystals are dried. There are obtained 1.5 g of 8-{2-oxo-2-[4-(quinol-2-ylmethoxy)phenyl]ethyl}-3,8-diaza-1-oxa-2-oxospiro[4,5]decane, m.p.(cap): 166°–170° C. Yield: 35%.

EXAMPLE 29

8-{[4-(quinol-2-ylmethoxy)phenyl]acetyl}-3,8-diaza-1-oxa-2-oxospiro[4,5]decane

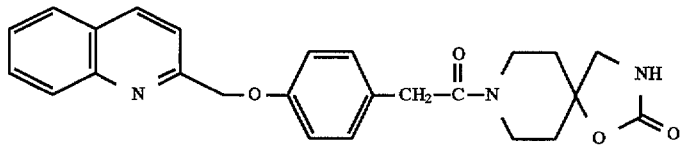

4.9 g of 4-benzyloxyphenylacetic acid (0.02 mol), 3.2 g of 3,8-diaza-1-oxa-2-oxospiro[4,5]decane, 12.7 ml of N-ethylmorpholine and 100 ml of dimethylformamide are introduced into a three-necked flask. The mixture is cooled to 5° C. 13.6 ml of 50% 1-propanephosphonic acid cyclic anhydride in methylene chloride (LANCASTER Ref.: 11911) are added. The mixture is stirred at 5° C. for 2 hours and then at room temperature for 16 hours. Water is added and the mixture is extracted with methylene chloride and washed with a 10% sodium hydrogen carbonate solution and then with a saturated lithium chloride solution. The mixture is dried over sodium sulphate and concentrated to dryness. There are obtained 7.8 g of 8-[(4-benzyloxy-phenyl)acetyl]-3,8-diaza-1-oxa-2-oxospiro[4,5]decane. Yield: 100%.

7.8 g of 8-[(4-benzyloxyphenyl)acetyl]-3,8-diaza-1-2-oxospiro[4,5]decane are hydrogenated in 200 ml of ethanol in the presence of 1.5 g of palladium hydroxide-on-carbon at 50° C. under 5×10$^5$ Pa. The catalyst is filtered off and concentration to dryness is carried out. The residue is recrystallised from 150 ml of ethanol. There are obtained 3.0 g of 8-[(4-hydroxyphenyl)acetyl]-3,8-diaza-1-oxa-2-oxospiro[4,5]decane. Yield: 50%.

2.7 g (0.0093 mol) de 8-[(4-hydroxyphenyl)acetyl]-3,8-diaza-1-oxa-2-oxospiro[4,5]decane, 2.2 g of 2-chloromethylquinoline hydrochloride, 2.8 g of potassium carbonate, 0.1 g of potassium iodide and 100 ml of dimethylformamide are introduced into a three-necked flask. Stirring is carried out at 40° C. for 16 hours. The mixture is concentrated to dryness. The residue is taken up in methylene chloride. The mixture is washed with a 10% sodium hydrogen carbonate solution and then with a saturated lithium chloride solution. It is dried over sodium sulphate and concentrated to dryness. The residue is chromatographed on 480 g of silica using a methylene chloride/methanol mixture (97/3) as eluant. The fractions that are of interest are concentrated to dryness and the residue is triturated in ethanol. Suction-filtration is carried out and the crystals are dried. There are obtained 3.0 g of 8-{[4-(quinolin-2-ylmethoxy)phenyl]acetyl}-3,8-diaza-1-oxa-2-oxospiro[4,5]decane, m.p.(cap): 182°–184° C. Yield: 75%.

EXAMPLE 30

By proceeding analogously to Example 20, the following compound was prepared:

8-[4-(quinol-2-ylmethoxy)benzoyl]-3,8-diaza-1-oxa-2-oxospiro[4,5]decane, m.p.(cap): 188°–190° C.

EXAMPLE 31

(R,S)-8-[2-(4-benzyloxyphenyl)-3-phenylpropyl]-3,8-diaza-1-oxa-2-oxospiro[4,5]decane hydrochloride

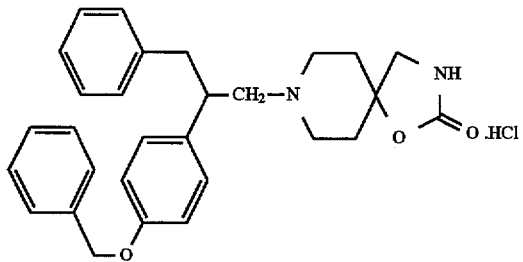

200 ml of liquid ammonia and 0.9 g of sodium are introduced into a three-necked flask. A crystal of iron(III) chloride is added and the mixture is stirred until the blue colouration has disappeared. 5 g of benzyl chloride dissolved in 50 ml of ether are added. The mixture is stirred for 24 hours until the ammonia has distilled off completely. The residue is taken up in ether, washed with water and dried over sodium sulphate. Concentration to dryness is carried out and the residue is chromatographed on 480 g of silica using a methylene chloride/cyclohexane mixture (50/50) as eluant. There are obtained 9.8 g of ethyl 2-(4-benzyloxyphenyl)-3-phenylpropionate. Yield: 63%.

9.5 g (0.026 mol) of ethyl 2-(4-benzyloxyphenyl)-3-phenylpropionate, 40 ml of toluene and 30 ml of methylene chloride are introduced into a three-necked flask. The mixture is cooled to −70° C. 44 ml of 1M diisobutylaluminium hydride in toluene are added over a period of 15 minutes. The mixture is stirred at that temperature for one hour. 30 ml of methanol and 60 ml of water are added at −70° C. The alumina is filtered off and the aqueous phase is extracted with methylene chloride. The combined organic phases are dried over sodium sulphate and concentrated to dryness. There are obtained 8.2 g of 2-benzyloxyphenyl-3-phenylpropionaldehyde. Yield: 100%.

8.0 g of 2-benzyloxyphenyl-3-phenylpropionaldehyde, 4 g of 3,8-diaza-1-oxa-2-oxospiro[4,5]decane, 12 g of sodium triacetoxyborohydride and 300 ml of methylene chloride are introduced into a three-necked flask. Stirring is carded out at room temperature for 16 hours. The mixture is washed with a saturated sodium hydrogen carbonate solution and dried over sodium sulphate. The organic phase is stirred in the presence of excess N hydrochloric acid. The mixture is suction-filtered and washed with ethanol. There are obtained 8 g of (R,S)-8-[2-(4-benzyloxyphenyl)-3-phenylpropyl]-3, 8-diaza-1-oxa-2-oxospiro[4,5]decane hydrochloride, m.p. (cap): 234°–236° C. Yield: 66%.

EXAMPLE 32

(R,S)-8-{3-phenyl-2-[4-(quinol-2-ylmethoxy)phenyl]propyl}-3,8-diaza-1-oxa-2-oxospiro[4,5]decane

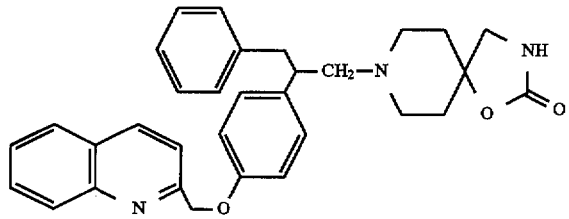

7 g of (R,S)-8-[2-(4-benzyloxyphenyl)-3-phenylpropyl]-3,8-diaza-1-oxa-2-oxospiro[4,5]decane hydrochloride (see Example 22) are hydrogenated in 400 ml of methanol and 1.5 g of palladium hydroxide-on-carbon under $5 \times 10^5$ Pa at 45° C. The mixture is filtered and concentrated to dryness. There are obtained 6.1 g of (R,S)-8-[2-(4-hydroxyphenyl)-3-phenylpropyl]-3,8-diaza-1-oxa-2-oxospiro[4,5]decane hydrochloride. Yield: 100%.

3.2 g (0.008 mol) of (R,S)-8-[2-(4-hydroxyphenyl)-3-phenylpropyl]-3,8-diaza-1-oxa-2-oxospiro[4,5]decane hydrochloride, 1.8 g of 2-chloromethylquinoline hydrochloride, 3.7 g of potassium carbonate, 0.25 g of potassium iodide and 100 ml of dimethylformamide are introduced into a three-necked flask. Stirring is carried out at 60° C. for 16 hours. The mixture is concentrated to dryness. The residue is taken up in methylene chloride and washed with a 10% sodium carbonate solution and then with a saturated lithium chloride solution. The mixture is dried over sodium sulphate and concentrated to dryness. The residue is chromatographed on 750 g of silica using a methylene chloride/methanol mixture (97/3) as eluant. There are obtained 2.5 g of (R,S)-8-{3-phenyl-2-[4-(quinol-2-ylmethoxy)phenyl]propyl}-3,8-diaza-1-oxa-2-oxospiro[4,5]decane, m.p.(cap): 154°–156° C. Yield: 69%.

EXAMPLES 32 TO 42

By proceeding analogously to Example 32, the following compounds were prepared:

33) (R,S)-8-{4-phenyl-2-[4-(quinol-2-ylmethoxy)phenyl]butyl}-3,8-diaza-1-oxa-2-oxospiro[4,5]decane, m.p. (cap): 72°–74° C.

34) (R,S)-8-{3-(4-chlorophenyl)-2-[4-(quinol-2-ylmethoxy)phenyl]propyl}-3,8-diaza-1-oxa-2-oxospiro[4,5]decane hydrochloride, m.p.(cap): 176°–180° C.

35) (R,S)-8-{3-(4-chlorophenyl)-2-[4-(5-phenylpyrid-2-ylmethoxy)phenyl]propyl}-3,8-diaza-1-oxa-2-oxospiro[4,5]decane, m.p.(cap): 172°–174° C.

36) (R,S)-8-{2-cyclopentyl-2-[4-(quinol-2-ylmethoxy)phenyl]ethyl}-3,8-diaza-1-oxa-2-oxospiro[4,5]decane hydrochloride, m.p.(cap): 240°–242° C.

37) (R,S)-8-{3-(4-chlorophenyl)-2-[4-(6-fluoroquinol-2-ylmethoxy)phenyl]propyl }-3,8-diaza-1-oxa-2-oxospiro[4,5]decane, m.p.(cap): 174°–176° C.

38) (R,S)-8-{4-(4-chlorophenyl)-2-[4-(6-fluoroquinol-2-ylmethoxy)phenyl]butyl}3,8-diaza-1-oxa-2-oxospiro[4,5-decane, m.p.(cap): 173°–175° C.

39) (R,S)-8-{4-(4-chlorophenyl)-2-[4-(quinol-2-ylmethoxy)phenyl]butyl}-3,8-diaza-1-oxa-2-oxospiro[4,5]decane, m.p.(cap): 175°–177° C.

40) (R,S)-8-{3-phenyl-2-[4-(quinol-2-ylmethoxy)phenyl]propyl}-3,8-diaza-1-oxa-2-thioxospiro[4,5]decane, m.p. (cap): 180°–185° C.

41) (R,S)-8-{3-phenyl-2-[4-(quinol-2-ylmethoxy)phenyl]propyl}-2,8-diaza-3-oxospiro[4,5]decane, m.p.(cap): 154°–156° C.

42) (R,S)-2-phenylethyl-8-{3-phenyl-2-[4-(quinol-2-ylmethoxy)phenyl]propyl}-2,8-diaza-1,3-dioxospiro[4,5]decane, m.p.(cap): 134°–136° C.

EXAMPLE 43

(R,S)-8-{cyclopentyl-[4-(quinol-2-ylmethoxy)phenyl]acetyl}-3,8-diaza-1-oxa-2-oxospiro[4,5]decane hydrochloride 3.6 g (0.01 mol) of [4-(quinol-2-ylmethoxy)phenyl]cyclopentylacetic acid (see European Patent Specification 034 45 19 A1), 1.6 g of 3,8-diaza-1-oxo-2-oxospiro[4,5]decane, 6.4 ml of N-ethylmorpholine and 50 ml of dimethylformamide are introduced into a three-necked flask. The mixture is cooled to 5° C., and 6.8 ml of 50% 1-propanephosphonic acid cyclic anhydride in methylene chloride (LANCASTER Ref.: 11911 ) are added. Stirring is carried out at 5° C. for 2 hours and then at room temperature for 48 hours. The mixture is concentrated to dryness and the residue is taken up in methylene chloride. The mixture is washed with a saturated sodium hydrogen carbonate solution and then with a saturated lithium chloride solution. It is dried over sodium sulphate and concentrated to dryness. The residue is chromatographed on 240 g of silica using a methylene chloride/methanol mixture (97/3) as eluant. The fractions that are of interest are concentrated to dryness and the residue is dissolved in ethanol. A slight excess of N hydrochloric acid is added. Crystallisation is seen to occur. The crystals are suction-filtered and dried at 60° C. under 67 Pa. There are obtained 3.2 g of (R,S)-8-{cyclopentyl-[4-(quinol-2-ylmethoxy)phenyl]acetyl}-3,8-diaza-1-oxa-2-oxospiro[4,5]decane hydrochloride, m.p.(cap): 200°–204° C. Yield: 60%.

EXAMPLE 44

PHARMACOLOGICAL STUDY

1/Method 1.1 Determination of 5-lipoxygenase-inhibiting activity in vitro (see Goldyne M. E., Burrish G. F., Poubelle P. and Borgeat P., *Arachidonic Acid Metabolism among human mononuclear leukocytes*. The Journal of Biological Chemistry. Vol. 259, N° 4, p. 8815–8819, 1984, and New Chang C. and Gin Wensu. *Stimulation of 5-Lipoxygenase Activity in Polymorphonuclear Leukocytes of Rats by Caseinate Treatment*. Biochemical Pharmacology. Vol. 36, N° 8, p. 3033–3036, 1987).

5-Lipoxygenase-inhibiting activity was determined on peritoneal leukocytes of rats. Leukocytosis is induced in male OFA rats (IFFA CREDO) weighing 200–250 g by the intraperitoneal injection of 12% sodium caseinate. 18 hours later, the cells are collected by washing the abdominal cavity. The number of cells is adjusted to $2 \times 10^6$/ml.

The cell suspension is incubated for 10 minutes at 37° C. in the presence of $Ca^{2+} 5 \times 10^{-4}$ M and $Mg^{2+} 2 \times 10^{-3}$ M and of various concentrations of the test products. The cells are then stimulated with the calcium ionophore A23187 at a concentration of $10^{-6}$ M for 5 minutes at 37° C. Controls are carded out by incubating the cells with the solvent for the products: 2% DMSO.

After stopping the reaction at +4° C. and centrifugation, the quantity of LTB4 in $ng/2 \times 10^6$ cells in the supernatants is determined by the E.I.A. method (Statlergenes France). The percentage inhibition is calculated as follows:

% inhibition =

$$\frac{\text{ng of LTB4 (solvent controls)} - \text{ng of LTB4 (for a concentration of product)}}{\text{ng of LTB4 (solvent controls)}} \times 100$$

1.2 Determination of 5-lipoxygenase-inhibiting activity ex vivo (see Brideau C., Chan C., Charleson S., Denis D. et al. *Pharmacology of MK*-0591 (3-[1-(4-chlorobenzyl)-3-(t-butyl-thio)-5(quinolin-2-yl-methoxy)-indol-2-yl]-2,2-dimethyl propanoic acid), a Potent, Orally Active Leukotriene Biosynthesis Inhibitor. Can. J. Physiol. Pharmacol. Vol. 70, p. 799–807, 1992).

Inhibition of the biosynthesis of leukotrienes ex vivo following oral administration of the compounds was determined by studying the production of leukotrienes on total blood of rats stimulated in vitro by the calcium ionophore at time 1 hour after oral administration of the compounds.

The various products are administered in suspension in hydroxyethylcellulose: 0.5% H.E.C. at a dose of 60 μmol/kg. Each product is studied on a group of 8 different animals. A control group receives 0.5% H.E.C. only. After intracardial removal of the blood from each rat (male Sprague Dawley rats weighing 150–200 g IFFA CREDO), 1 ml of heparinised blood is incubated with the calcium ionophore A23 187 at a concentration of $5 \times 10^{-5}$ M for 10 minutes at 37° C. The blood is then centrifuged immediately and 100 μl of plasma are extracted in 400 μl of methanol. After centrifugation, the supernatant is evaporated to dryness under $N_2$, the dry residue is taken up in buffer solution, and the LTB4 is assayed by the E.I.A. method (Stallergenes France).

The percentage inhibition is expressed as follows:

% inhibition =

$$\frac{\text{ng of LTB4/1 ml of blood (control group)} - \text{ng of LTB4/1 ml of blood (treated group)}}{\text{ng of LTB4/1 ml of blood (control group)}} \times 100$$

2/Results

The results are given in the Tables below.

TABLE 1

Inhibition of the synthesis of LTB4 and PGE2 by the peritoneal PMN of rats in vitro

| Products of ex. | n | LTB4 % Inhibition $10^{-8}$ M | $4 \cdot 10^{-8}$ M | $10^{-7}$ M | $10^{-6}$ M | $10^{-5}$ M | IC50 | n | PGE2 % Inhibition $10^{-5}$ M | $10^{-4}$ M | IC50 |
|---|---|---|---|---|---|---|---|---|---|---|---|
| 1 | | | | | | | $2 \cdot 10^{-5}$ M | | | | |
| 2 | | | | | 90% | | $6 \cdot 10^{-7}$ M | 1 | | 23% | $>10^{-4}$ M |
| 3 | | | | | | | $>10^{-4}$ M | | | | |
| 4 | | | | | | | $>1.6 \cdot 10^{-6}$ M | | | | |
| 5 | | | | 15% | 95% | | $3 \cdot 10^{-7}$ M | 1 | | | $>10^{-4}$ M |
| 6 | 3 | 21% | 60% | 93% | 100% | | $3.1 \cdot 10^{-8}$ M | 1 | 3% | 88% | $10^{-5}$ M $\ll 10^{-4}$ M |
| 7 | 1 | | | 36% | | | $>10^{-6}$ M | | | | |
| 8 | 3 | 22% | 85% | 100% | 100% | | $1.7 \cdot 10^{-8}$ M | 1 | 32% | 72% | $10^{-5}$ M $\ll 10^{-4}$ M |
| 9 | 1 | | | | | | $>10^{-7}$ M | | | | |
| 10 | 1 | | | 28% | | 92% | $>10^{-7}$ M | | | | |
| 11 | 1 | | | 38% | | 76% | $>10^{-7}$ M | | | | |
| 12 | 1 | | | 53% | 98% | | $10^{-7}$ M | 1 | 92% | 86% | $<10^{-5}$ M |
| 13 | 1 | | | 21% | | 91% | $>10^{-7}$ M | | | | |
| 22 | 3 | 18% | 76% | 97% | 100% | | $2 \cdot 10^{-8}$ M | 1 | 6% | 4% | $>10^{-4}$ M |
| 23 | 1 | | | 9% | | | $>10^{-6}$ M | | | | |
| 24 | 1 | | 56% | 100% | | | $3.6 \cdot 10^{-8}$ M | 1 | 19% | 44% | $>10^{-4}$ M |
| 25 | | | | 8% | 7% | | $>1.6 \cdot 10^{-6}$ M | | | | |
| 26 | 1 | | | | | | $>10^{-7}$ M | | | | |
| 28 | 1 | | | | 37% | | $>10^{-6}$ M | | | | |
| 29 | 1 | | | 30% | 18% | | $>10^{-6}$ M | | | | |
| 30 | 1 | | | | 14% | | $>10^{-6}$ M | | | | |
| 31 | 1 | | | | 16% | | $>10^{-6}$ M | | | | |
| 32 | 3 | | 24% | 78% | 100% | | $6.2 \cdot 10^{-8}$ M | 1 | | 92% | $10^{-5}$ M $\ll 10^{-4}$ M |
| 33 | 2 | 6% | 54% | 86% | | | $4.9 \cdot 10^{-8}$ M | 1 | 7% | 94% | $10^{-5}$ M $\ll 10^{-4}$ M |
| 34 | 2 | 12% | 56% | 72% | 100% | | $3.9 \cdot 10^{-8}$ M | 1 | 2% | 6% | $>10^{-4}$ M |
| 35 | 1 | | | | | | $>10^{-6}$ M | | | | |
| 36 | 1 | | | | | | $>10^{-7}$ M | | | | |
| 43 | 1 | | | 8% | | | $>10^{-7}$ M | | | | |

Operating conditons:
Metabolism of arachidonic acid by the peritoneal PMN of rats stimulated for 5 minutes in vitro by the calcium ionophore (A23187): $10^{-6}$ M.
Incubation of the products with the cells for 10 minutes prior to stimulation with the ionophore.
Assay of LTB4 by EIA.
Reference product:
When tested under the same conditions, fenspiride or 8-(2-phenylethyl)-3,8-diaza-1-oxa-2-oxospiro[4,5]decane is inactive at a dose of $10^{-4}$ M.

TABLE 2

Inhibition of the synthesis of LTB4 in total blood of rats ex vivo, 1 h

| Products of Examples (60 μmol/kg p.o.) | % Inhibition |
|---|---|
| 6 | 64% |
| 8 | 46% |
| 22 | 17% |

TABLE 2-continued

Inhibition of the synthesis of LTB4 in total blood of rats ex vivo, 1 h

| Products of Examples (60 µmol/kg p.o.) | % Inhibition |
| --- | --- |
| 24 | 41% |
| 32 | 55% |
| 33 | 48% |
| 34 | 58% |

Operating conditions:
Average relative to all controls n = 31
Products administered p.o. 1 hour before removal of blood n = 8
Total blood of rats stimulated for 10 minutes in vitro by the calcium ionophore A23187: 5 × 10−5 M
Assay of LTB4 by EIA.

We claim:

1. An 8-{[4-(quinol-2ylmethoxy)phenyl]lower-alkylene}-3,8-diaza-1-oxa-2-oxospiro[4,5]decane selected from the group consisting of those of formula I:

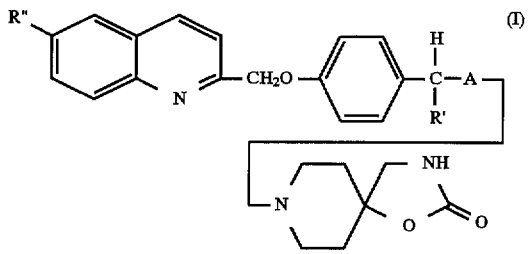

in which:

R" is selected from the group consisting of hydrogen and halogen;

R' is selected from the group consisting of hydrogen, ($C_1$–$C_5$) alkyl, phenyl, halophenyl, benzyl, halobenzyl, halophenethyl, and cyclopentyl; and A is selected from the group consisting of a single bond and ($C_1$–$C_5$) straight hydrocarbon chains;

the corresponding enantiomers and diastereoisomers thereof, and the physiologically-tolerable salts thereof with an acid.

2. A compound of claim 1 which is (R,S)-8-{2-phenyl-2-[4-(quinol-2-ylmethoxy)phenyl]-ethyl}-3,8-diaza-1-oxa-2-oxospiro[4,5]decane, of its hydrochloride.

3. A compound of claim 1 which is (R,S)-8-{2-(4-chlorophenyl)-2-[4-(quinol-2-ylmethoxy)-phenyl]ethyl}-3,8-diaza-1-oxa-2-oxospiro[4,5]decane, or its dihydrochloride.

4. A compound of claim 1 which is (R,S)-8-{(4-chlorophenyl)-[4-(quinol-2-ylmethoxy)-phenyl]methyl}-3,8-diaza-1-oxa-2-oxospiro[4,5]decane, or its dihydrochloride.

5. A compound of claim 1 which is (R,S)-8-{phenyl-[4-(quinol-2-ylmethoxy)phenyl]methyl}-3,8-diaza-1-oxa-2-oxospiro[4,5]decane.

6. A compound of claim 1 which is (R,S)-8-{3-phenyl-2-[4-(quinol-2-ylmethoxy)phenyl]-propyl}-3,8-diaza-1-oxa-2-oxospiro[4,5]decane.

7. A compound of claim 1 which is (R,S)-8-{4-phenyl-2-[4-(quinol-2-ylmethoxy)phenyl]-butyl}-3,8-diaza-1-oxa-2-oxospiro[4,5]decane.

8. A compound of claim 1 which is (R,S)-8-{3-(4-chlorophenyl)-2-[4-(quinol-2-ylmethoxy)-phenyl]propyl}-3,8-diaza-1-oxa-2-oxospiro[4,5]decane, or hydrochloride.

9. A method for treating a living animal body afflicted with a pathology which is treatable by producing an inhibitory effect on the enzyme 5-lipoxygenase comprising the step of administering to the living animal body an amount of a compound of claim 1 which is effective for alleviation of said pathology.

10. A pharmaceutical composition useful in the treatment of a pathology which is treatable by producing an inhibitory effect on the enzyme 5-lipoxygenase, comprising as active ingredient at least one of the compounds according to claim 1 together with one or more pharmaceutically-acceptable excipients.

* * * * *

UNITED STATES PATENT AND TRADEMARK OFFICE
CERTIFICATE OF CORRECTION

PATENT NO. : 5,698,567
DATED : Jan. 16, 1997                                    Page 1 of 3
INVENTOR(S) : C. Guillonneau, Y, Charton, G. Regnier, E. Canet, M. Lonchampt It is certified that error appears in the above-indentified patent and that said Letters Patent is hereby corrected as shown below:

Column 4, line 53: "carded" should read -- carried --.

Column 4, line 56: "arthydride" should read -- anhydride --.

Column 11, line 32: tdphenylphosphine" should read -- triphenylphosphine --.

Column 11, line 33: "carded" should read -- carried --.

Column 11, line 38: "carded" should read -- carried --.

Column 11, line 51: ":3,8-diaza-1-2" should read -- -3,8-diaza-1-oxa-2- --.

Column 11, line 58: At the beinning of the line, Insert -- oxa- -- before the "2-".

Column 12, line 39: "carded" should read -- carried --.

Column 12, line 44: After "There are obtained", Insert -- 14.5g of --.

Column 12, line 56: "carded" should read -- carried --.

UNITED STATES PATENT AND TRADEMARK OFFICE
CERTIFICATE OF CORRECTION

PATENT NO. : 5,698,567
DATED : Jan. 16, 1997
INVENTOR(S) : C. Guillonneau, Y, Charton, G. Regnier, E. Canet, M. Lonchampt Page 2 of 3

It is certified that error appears in the above-indentified patent and that said Letters Patent is hereby corrected as shown below:

Column 13, line 52: "suction-faltered" should read -- suction-filtered --.

Column 14, line 65: "R.S.)-" should read -- (R.S.)- --.

Column 16, line 37: "162-20-164°C." should read -- 162-164°C. --.

Column 17, line 36: At the end of the line, "-3,8-diaza-1-2-" should read -- -3,8-diaza-1-oxa-2- --.

Column 18, line 61: "carded" should read -- carried --.

Column 19, line 40: "EXAMPLES 32 TO 42" should read -- EXAMPLES 33 TO 42 --.

Column 21, line 66: "A23 187" should read -- A23187 --.

UNITED STATES PATENT AND TRADEMARK OFFICE
CERTIFICATE OF CORRECTION

PATENT NO. : 5,698,567
DATED : Jan. 16, 1997
INVENTOR(S) : C. Guillonneau, Y, Charton, G. Regnier, E. Canet, M. Lonchampt It is certified that error appears in the above-indentified patent and that said Letters Patent is hereby corrected as shown below:

Column 24, line 6: "of its hydrochloride" should read -- or its hydrochloride --. Preliminary Amendment dtd 5/16/96, Claim 2, line 2

Column 24, line 25: "or hydrochloride" should read -- or its hydrochloride --. Page 29, Claim 8, line 20

Signed and Sealed this

Twenty-seventh Day of October, 1998

Attest:

BRUCE LEHMAN

Attesting Officer

Commissioner of Patents and Trademarks